(12) United States Patent
David et al.

(10) Patent No.: US 10,799,337 B2
(45) Date of Patent: Oct. 13, 2020

(54) IMPERMEABLE INNER SHELL FOR A BREAST IMPLANT

(71) Applicant: BIOSENSE WEBSTER (ISRAEL) LTD., Yokneam (IL)

(72) Inventors: Dganit David, Moshav Ahituv (IL); Yehuda Algawi, Binyamina (IL); Assaf Govari, Haifa (IL); Ilya Sitnitsky, Nahariya (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 113 days.

(21) Appl. No.: 15/917,291

(22) Filed: Mar. 9, 2018

(65) Prior Publication Data
US 2019/0274820 A1    Sep. 12, 2019

(51) Int. Cl.
*A61F 2/12* (2006.01)
*A61L 27/26* (2006.01)
*A61L 27/28* (2006.01)
*A61L 27/30* (2006.01)

(52) U.S. Cl.
CPC .............. *A61F 2/12* (2013.01); *A61L 27/26* (2013.01); *A61L 27/28* (2013.01); *A61L 27/306* (2013.01); *A61F 2240/001* (2013.01); *A61F 2250/0003* (2013.01); *A61L 2420/02* (2013.01); *A61L 2430/04* (2013.01)

(58) Field of Classification Search
CPC combination set(s) only.
See application file for complete search history.

(56) References Cited

U.S. PATENT DOCUMENTS

| 4,125,117 | A | * | 11/1978 | Lee ........................... A61F 2/52 450/54 |
| 5,376,117 | A | | 12/1994 | Pinchuk |
| 9,486,309 | B2 | | 11/2016 | Schuessler |
| 2006/0069403 | A1 | * | 3/2006 | Shalon ...................... A61F 2/12 606/192 |
| 2007/0093911 | A1 | | 4/2007 | Fricke et al. |
| 2009/0099656 | A1 | | 4/2009 | Gelda et al. |
| 2009/0210056 | A1 | | 8/2009 | Forsell |
| 2012/0277860 | A1 | | 11/2012 | Dvir et al. |
| 2014/0197355 | A1 | * | 7/2014 | Ram .................. C08G 73/1035 252/75 |
| 2016/0256295 | A1 | | 9/2016 | Wollnick et al. |

FOREIGN PATENT DOCUMENTS

| WO | WO 2011/058550 A1 | 5/2011 |
| WO | WO 2015/132158 A1 | 9/2015 |

OTHER PUBLICATIONS

PCT/IB2019/051932—International Search Report dated Jun. 18, 2019.

* cited by examiner

*Primary Examiner* — Yashita Sharma
(74) *Attorney, Agent, or Firm* — Eugene L. Szczecina, Jr.

(57) ABSTRACT

An implantable device includes a first sealed flexible shell configured for implantation within a breast of a human subject, an elastic filler material contained within the first sealed flexible shell, and a second sealed flexible, inelastic shell, which is disposed within the elastic filler material inside the first sealed flexible shell and is inflated with a volume of gas. The second shell includes a material selected such that an amount of the gas escaping from the second shell does not exceed $10^{-8}$ Torr-liter/second when the gas pressure inside the second shell is 250 mbar higher than the gas pressure outside the second shell.

8 Claims, 9 Drawing Sheets

IMPERMEABLE INNER SHELL FOR A BREAST IMPLANT

FIELD OF THE INVENTION

The present invention relates generally to medical devices, and particularly to breast implants.

BACKGROUND

A breast implant is either inserted in a human breast or attached on the breast in order to replace tissue that has been medically removed in an operation such as a mastectomy. The purpose of the breast implant is to restore to the breast its external form, including its tactile feel and weight. A breast implant may also be inserted in a breast to enhance or enlarge the appearance of the breast for cosmetic purposes.

PCT Patent Application WO2015132158 describes a medical implant which is vacuum-packed within an air tight cover material.

U.S. Patent Application 2007/0093911 describes a soft tissue implant such as a breast implant, which comprises an external shell-type envelope of flexible plastic material, in particular of silicone, a liquid to viscous filler material contained in the envelope, and a metal-containing, biocompatible, continuous coating on the outside of the envelope.

PCT Patent Application WO2011058550 describes a breast implant comprising an envelope and a filling, and wherein the filling comprises a gaseous phase.

U.S. Patent Application 2009/0099656 describes a breast implant with outer spherical layers, layer of silicone gel and an inner core of gas filled silicon spheres.

U.S. Patent Application 2012/0277860 describes a prosthetic implant material for use in a prosthetic implant, comprising a gel and optionally a gas.

U.S. Pat. No. 5,376,117 describes a breast implant including an outer shell having a smooth non-porous outer envelope and a non-woven porous outer layer affixed to the envelope.

SUMMARY

Embodiments of the present invention that are described hereinbelow provide for an improved breast implant.

There is therefore provided, in accordance with an embodiment of the present invention, an implantable device, which includes a first sealed flexible shell configured for implantation within a breast of a human subject, an elastic filler material contained within the first sealed flexible shell, and a second sealed flexible, inelastic shell, which is disposed within the elastic filler material inside the first sealed flexible shell and is inflated with a volume of a gas. The second shell is constructed of a substance impermeable to the gas, such that an amount of the gas escaping from the second shell does not exceed $10^{-8}$ Torr-liter/second when the gas pressure inside the second shell is 250 mbar higher than the gas pressure outside the second shell.

In an embodiment the second sealed flexible, inelastic shell includes a first composite of polyamide and polyurethane, and a second composite of polyurethane and ethylene vinyl alcohol.

In another embodiment at least one coating impermeable to the gas is deposited on the second shell. The coating includes graphene oxide, aluminum oxide, or titanium oxide.

In another embodiment the elastic filler material includes silicone gel.

In a further embodiment the volume of gas includes a volume of air or argon.

There is also provided, in accordance with an embodiment of the present invention, an implantable device, which includes a first sealed flexible shell configured for implantation within a breast of a human subject, an elastic filler material contained within the first sealed flexible shell, and a second sealed flexible, inelastic shell. The second sealed flexible, inelastic shell is disposed within the elastic filler material inside the first sealed flexible shell and is inflated with a volume of a gas, and the second shell includes a first composite layer of polyamide and polyurethane overlaying which is cemented to a second composite layer of polyurethane, ethylene vinyl alcohol, and polyethylene.

There is further provided, in accordance with an embodiment of the present invention, an implantable device, which includes a first sealed flexible shell configured for implantation within a breast of a human subject, an elastic filler material contained within the first sealed flexible shell, and a second sealed flexible, inelastic shell. The second sealed flexible, inelastic shell is disposed within the elastic filler material inside the first sealed flexible shell and includes at least one coating including at least one of aluminum oxide, titanium oxide, and graphene oxide is deposited on the second shell.

There is also provided, in accordance with an embodiment of the present invention, a method for manufacturing an implantable device, the method including providing a first sealed flexible shell configured for implantation within a breast of a human subject, filling the first sealed flexible shell with an elastic filler material, providing a second sealed flexible, inelastic shell which is impermeable to a gas, such that an amount of the gas escaping from the second shell does not exceed $10^{-8}$ Torr-liter/second when the gas pressure inside the second shell is 250 mbar higher than the gas pressure outside the second shell, disposing the second shell within the elastic filler material inside the first sealed flexible shell, and inflating the second shell with a volume of the gas.

In an embodiment the second sealed flexible, inelastic shell includes a first composite of polyamide and polyurethane, and a second composite of polyurethane, ethylene vinyl alcohol, and polyethylene.

In a further embodiment providing a second sealed flexible shell impermeable to a gas includes depositing at least one coating impermeable to the gas on the second shell.

In an embodiment the coating includes graphene oxide, and depositing the coating includes providing graphene oxide as a suspension in a liquid, applying the liquid on an outer surface of the second shell, and allowing the liquid to dry.

In another embodiment the coating includes aluminum oxide, and depositing the coating includes providing aluminum oxide as a suspension in a liquid, applying the liquid on an outer surface of the second shell, and allowing the liquid to dry.

In yet another embodiment the coating includes titanium oxide, and depositing the coating includes providing titanium oxide as a suspension in a liquid, applying the liquid on an outer surface of the second shell, and allowing the liquid to dry.

In an embodiment filling the first sealed flexible shell includes filling the shell with silicone gel.

In another embodiment inflating the second sealed flexible shell includes inflating the shell with air or argon.

The present invention will be more fully understood from the following detailed description of the embodiments thereof, taken together with the drawings in which:

DETAILED DESCRIPTION OF EMBODIMENTS

Overview

A commonly used breast implant is an implant wherein an elastic filler material, such as silicone gel, is contained in a first sealed flexible shell. However, a breast implant that is completely filled with such a material is relatively heavy, and may cause discomfort to the wearer of the implant.

Embodiments of the present invention provide an implantable device that is used as a breast implant. The device comprises a first sealed flexible shell that is configured for implantation within a breast of a human subject. An elastic filler material is contained within the first flexible shell.

There is a second sealed, flexible, inelastic shell that is disposed within the elastic filler material with a volume of gas within the second shell, wherein the second shell is impermeable to the gas.

Embodiments of the present invention that are described herein address the potential for gas leakage from the second shell so as to enable the construction of a breast implant equipped with a balloon-like second shell with no appreciable gas leakage over the lifetime of the implant. This enables the construction and fabrication of light-weight and stable breast implants.

The disclosed embodiments use gas-impermeable composite materials for constructing the second shell. A material is deemed impermeable to gas if the amount of gas escaping from a closed shell constructed of the material typically does not exceed $10^{-8}$ Torr-liter/second for an overpressure of 250 mbar within the shell. In alternative disclosed embodiments gas-impermeable coatings are deposited on the second shell, with the above definition of gas-impermeability applied to the coatings. The disclosed embodiments reduce any potential gas leakage to ensure a usable life-time of approximately 10 years for a breast implant.

System Description

Figure 1:
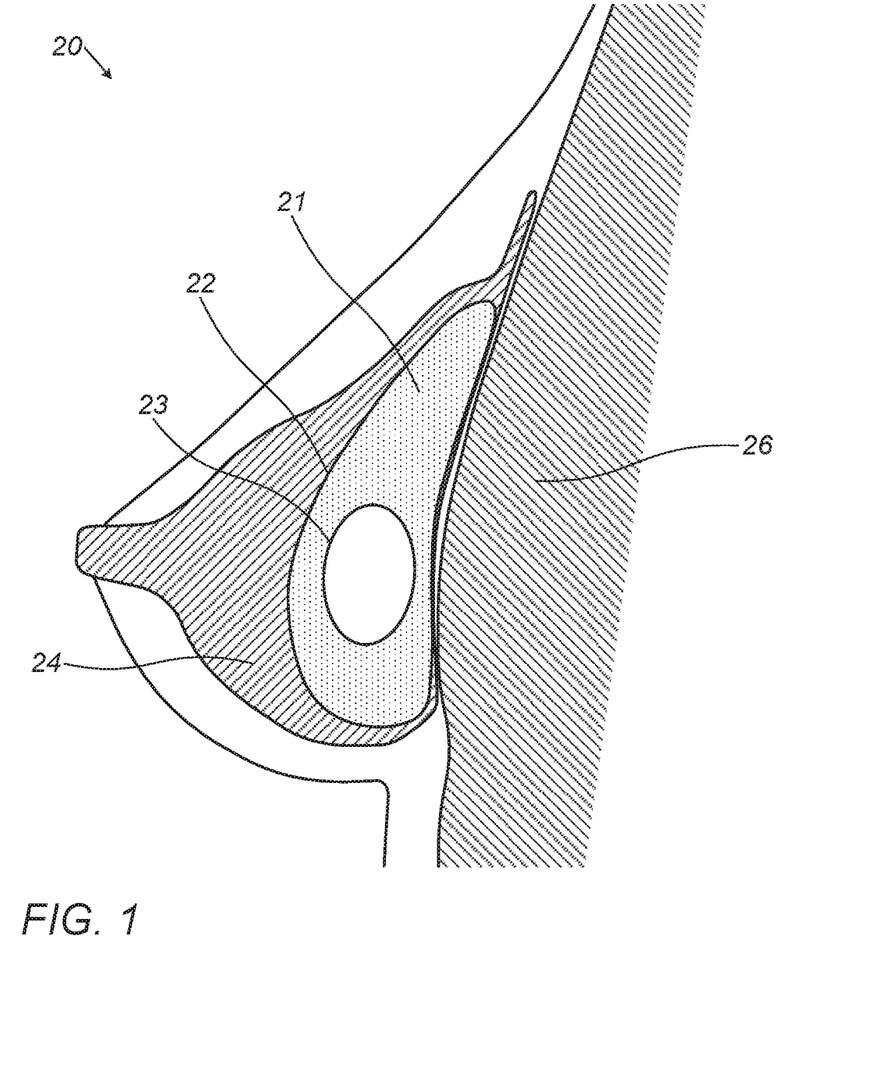
FIG. 1 is a schematic sectional illustration of a human female breast with a breast implant, in accordance with an embodiment of the invention.

FIG. 1 is a schematic sectional illustration of a human female breast 20 with a breast implant 21, in accordance with an embodiment of the present invention. Implant 21 comprises a first shell 22 and a second shell 23, described in more detail below. In the disclosed embodiment, breast implant 21 is positioned as a subglandular implant between breast tissue 24 and a pectoralis major muscle 26. In alternative embodiments, breast implant 21 may be positioned either as a subfascial, subpectoral, or submuscular implant, referring to different positions of the implant relative to pectoralis major muscle 26, as will be understood by those skilled in the art.

Figure 2:
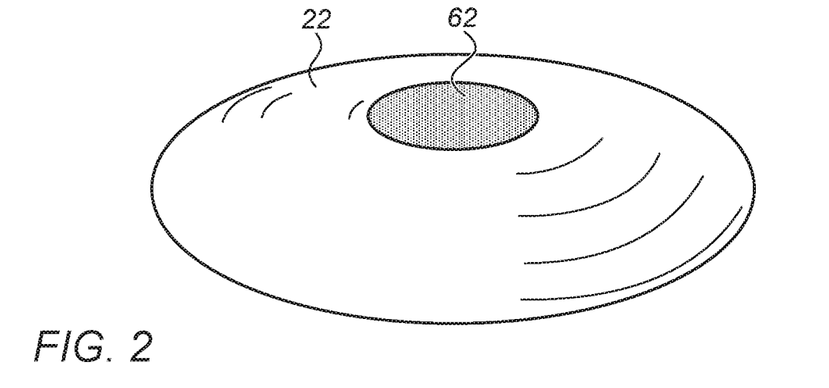
FIG. 2 is a schematic perspective view of a first shell of the breast implant, in accordance with an embodiment of the invention.

FIG. 2 is a schematic perspective view of first shell 22 of breast implant 21, in accordance with an embodiment of the invention. First shell 22 is fabricated by repeatedly dipping a mandrel (not shown) in a silicone solution. The coat of the silicone solution is allowed to solidify between consecutive dips. Once a sufficient thickness of the silicone layer covering the mandrel, typically 0.1 mm, has been reached and the silicone has solidified, the silicone "skin" is peeled off the mandrel. An opening 62 is left in first shell 22 by the stem of the mandrel.

Figure 3:
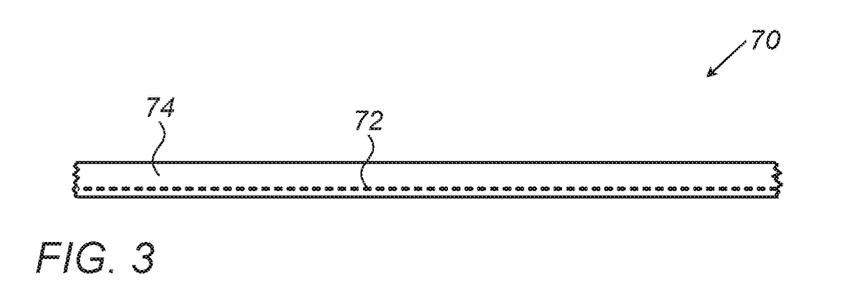
FIG. 3 is a schematic sectional view of PA/PU (polyamide/polyurethane) composite material, in accordance with an embodiment of the invention.

FIG. 3 is a schematic sectional view of a PA/PU (polyamide and polyurethane) composite material 70, in accordance with an embodiment of the invention. PA/PU composite material 70, which is a flexible and inelastic, is used for second shell 23. Alternatively, other flexible and inelastic materials may be used. The flexibility of second shell 23 allows the shell to adapt its shape to the changing shape of implant 21 due to e.g. movement of breast 20. The inelasticity of second shell 23 prevents the shell, and thus implant 21, from changing its size in a low-pressure environment, such as inside an airplane.

Composite material 70 is fabricated by dipping a fine net of PA (polyamide) 72 in a liquid form of PU (polyurethane) 74. The composite is then fed through two parallel rollers to flatten out the sheet.

Figure 4:
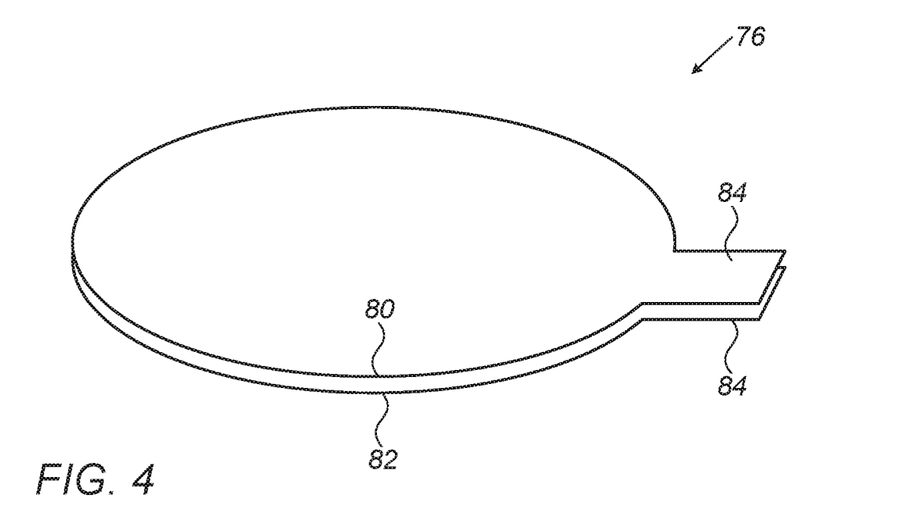
FIG. 4 is a schematic perspective view of cut PA/PU composite material prepared for RF (radio frequency) welding, in accordance with an embodiment of the invention.

FIG. 4 is a schematic perspective view of PA/PU composite material 70 after it has been cut in preparation for radio frequency (RF) welding, in accordance with an embodiment of the invention. Two similarly shaped pieces have been cut out of PA/PU composite material 70, forming an upper composite sheet 80 and a lower composite sheet 82 that together form a second shell preform 76. As described below sheets 80 and 82 are used to form second shell 23, and the shape of sheets 80 and 82 may be circular, square, or any other desired shape for second shell 23. An extension 84 is left on each part to form a fill tube 86 (shown in FIG. 5) after RF welding.

Figure 5:
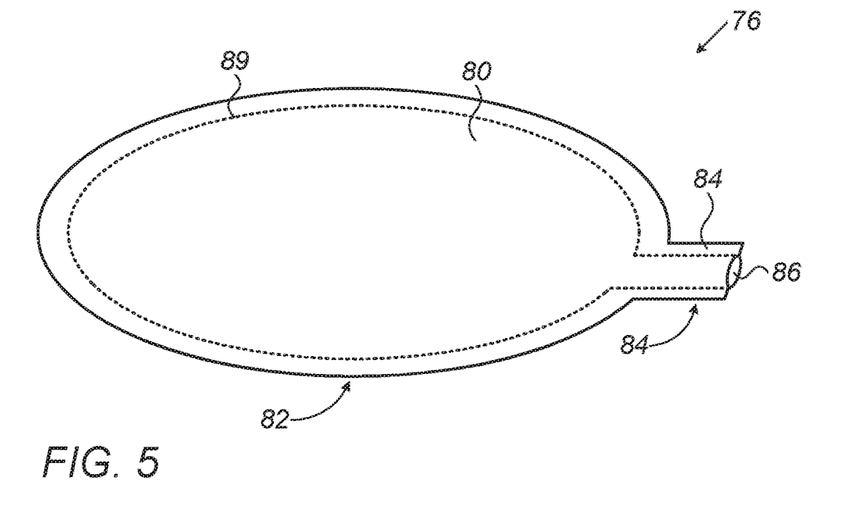
FIG. 5 is a schematic perspective view of a second shell preform after RF welding of two pieces of PA/PU composite material, in accordance with an embodiment of the invention.

FIG. 5 is a schematic perspective view of second shell preform 76 after RF welding of upper and lower composite sheets 80 and 82, respectively, in accordance with an embodiment of the invention. Upper and lower composite sheets 80 and 82, respectively, have been RF welded together along a weld line 89 positioned at the perimeters of the sheets. In the process, a fill tube 86 has been formed from extensions 84, to be used for inflating second shell preform 76.

FIGS. 6-12 show the construction of second shell 23 using a layer of ethylene-vinyl-alcohol, in accordance with an embodiment of the invention.

Figure 6:
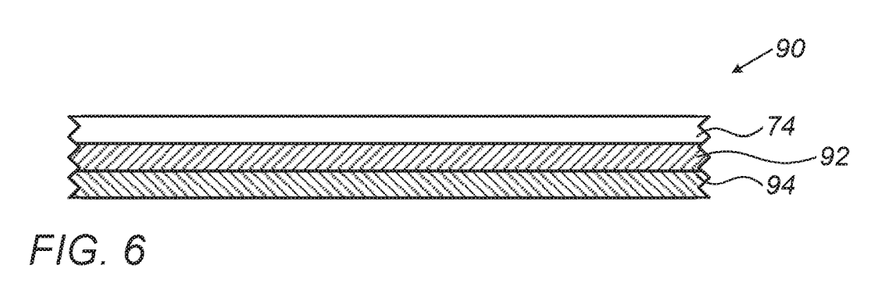
FIG. 6 is a schematic sectional view of a PU/EVOH/PE (polyurethane/ethylene-vinyl-alcohol/polyethylene) composite material, in accordance with an embodiment of the invention.

FIG. 6 is a schematic sectional view of a composite material 90, in accordance with an embodiment of the invention. In one embodiment composite material 90 comprises a composite of polyurethane and ethylene-vinyl-alcohol and polyethylene (PU/EVOH/PE) which is used for covering PA/PU composite material 70 and thus reducing its permeability to gas. PU/EVOH/PE composite material 90 comprises PU layer 74, an EVOH layer 92, and a PE layer 94.

Alternatively, composite 90 comprises a composite of polyurethane and ethylene-vinyl-alcohol (PU/EVOH) and PU/EVOH may be used instead of PU/EVOH/PE composite to cover PA/PU composite material 70.

Figure 7:
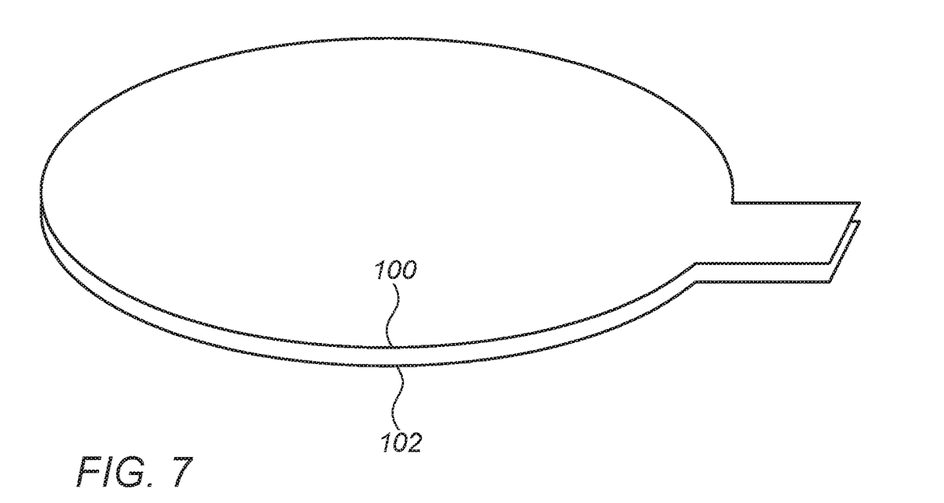
FIG. 7 is a schematic perspective view of PU/EVOH/PE composite material after it has been cut in preparation for cementing to the second shell preform, in accordance with an embodiment of the invention.

FIG. 7 is a schematic perspective view of PU/EVOH/PE composite material 90 after it has been cut in preparation for cementing to second shell preform 76, in accordance with an embodiment of the invention. Two similarly shaped sheets 100 and 102 have been cut out of PU/EVOH/PE composite material 90. The shapes and sizes of sheets 100 and 102 are chosen to cover second shell preform 76 of FIG. 5, with a sufficient margin to permit RF welding outside the preform.

Figure 8:
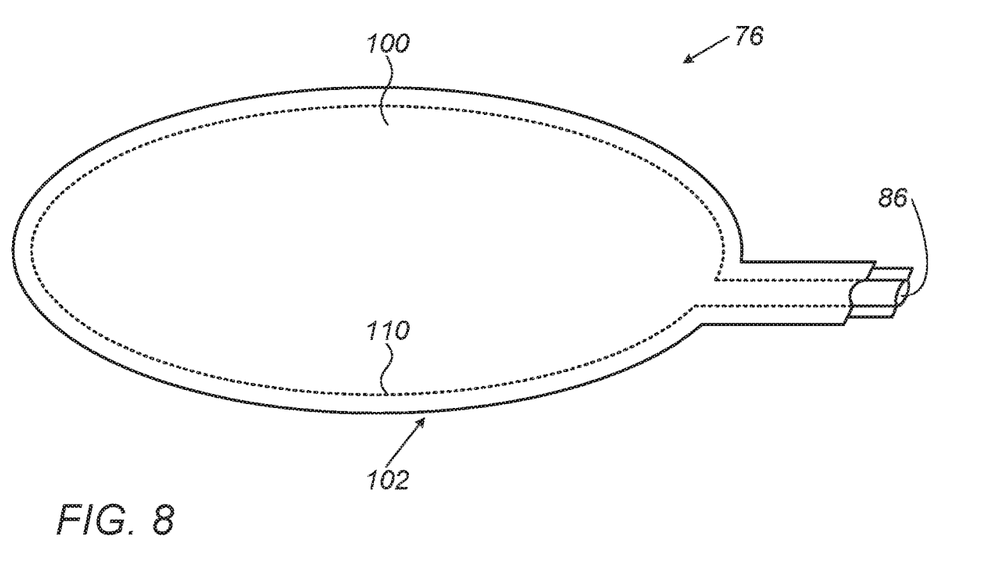
FIG. 8 is a schematic perspective view of the second shell preform after cementing PU/EVOH/PE composite material sheets onto PA/PU composite material and attaching to each other upper and lower sheets by RF welding, in accordance with an embodiment of the invention.

FIG. 8 is a schematic perspective view of second shell preform 76 after cementing sheets 100 and 102 of PU/EVOH/PE composite material 90 onto PA/PU composite material 70 and attaching to each other upper and lower sheets 100 and 102, respectively, by RF welding, in accordance with an embodiment of the invention. Upper and lower sheets 100 and 102, respectively, have been RF welded together along a weld line 110 positioned at the perimeters of the sheets and outside the extent of sheets 80 and 82 of FIG. 5. Fill tube 86 is still left accessible for inflating second shell preform 76.

Figure 9:
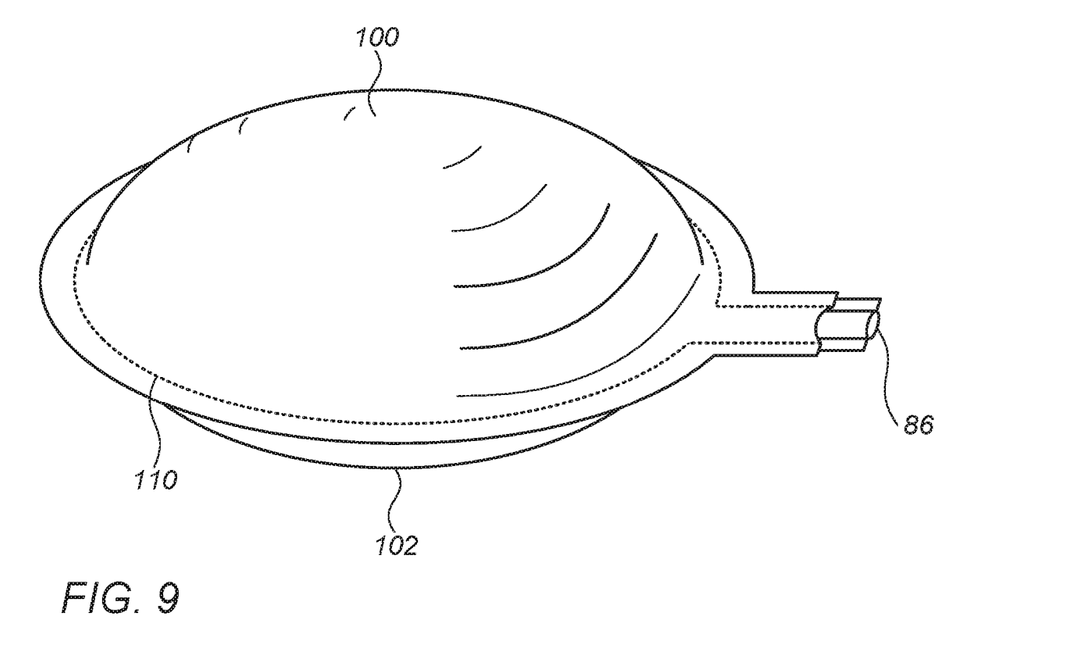
FIG. 9 is a schematic perspective view of the second shell preform after the preform has been inflated with air or other gas, in accordance with an embodiment of the invention.

FIG. 9 is a schematic perspective view of second shell preform 76 after the preform has been inflated with air or other gas, in accordance with an embodiment of the invention. Upper composite sheets 80 together with 100 and lower composite sheets 82 together with 102, respectively, have formed a balloon-like volume due to the inflation of second shell preform 76 through fill tube 86. Only sheets 100 and 102 are visible in FIG. 9, as sheets 80 and 82 are on the inside of the balloon-like volume.

Figure 10:
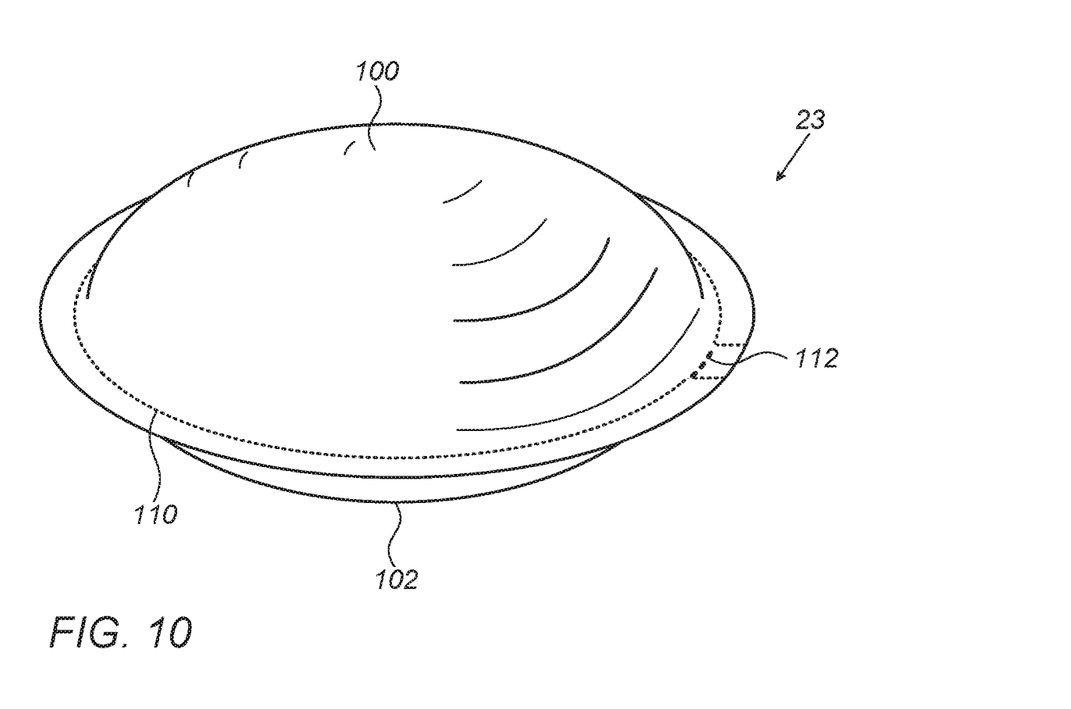
FIG. 10 is a schematic perspective view of a completed second shell formed from the preform, in accordance with an embodiment of the invention.

FIG. 10 is a schematic perspective view of completed second shell 23 formed from preform 76, in accordance with an embodiment of the invention. RF weld 110 has been completed with a sealing RF weld 112, thus completely sealing off the gas volume within the balloon-like volume. In addition, the part of fill tube 86 outside the edge of second shell preform 76 has been cut off.

In alternative embodiments, other methods, such as cementing, may be used instead of RF welding for attaching upper and lower sheets 80 and 82 and upper and lower sheets 100 and 102 to each other.

Based on the inventors' experiments with a 250 mbar overpressure of oxygen inside completed second shell 23, the leakage was found to be $10^{-9}$ Torr-liter/second, yielding an estimated usable life-time exceeding 10 years for completed second shell 23 inside a breast implant. Inflating completed second shell 23 with argon instead of air or oxygen may reduce the leakage even further.

Figure 11:
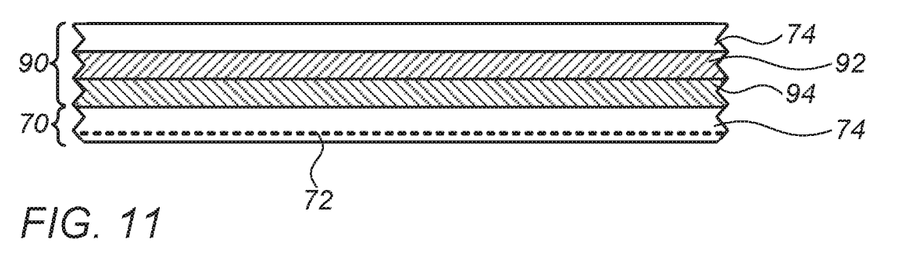
FIG. 11 is a schematic sectional view of PU/EVOH/PE composite material cemented onto one side of PA/PU composite material, in accordance with an embodiment of the invention.

FIG. 11 is a schematic sectional view of PU/EVOH/PE composite material 90 covering PA/PU composite material 70, in accordance with an embodiment of the invention. PU/EVOH/PE composite material 90 may be cemented or otherwise attached to PA/PU composite material 70. The thicknesses of the components of PA/PU composite material 70 (PA 72 and PU 74) in the figure, as well as those of the components of PU/EVOH/PE composite material 90 (PU 74, EVOH 92, and PE 94), are not to scale. Typical thicknesses of the components are 0.5-1.5 mm.

Figure 12:
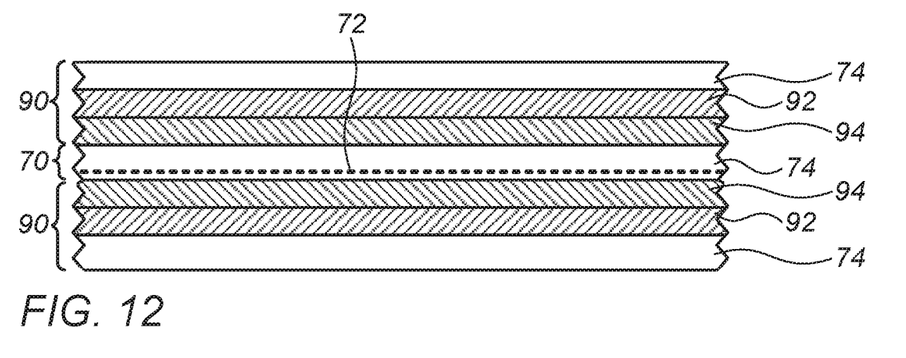
FIG. 12 is a schematic sectional view of PU/EVOH/PE composite material cemented onto both sides of PA/PU composite material, in accordance with an alternative embodiment of the invention.

FIG. 12 is a schematic sectional view of PU/EVOH/PE composite material 90 covering both sides of PA/PU composite material 70, in accordance with an embodiment of the invention. PU/EVOH/PE composite material 90 may be cemented or otherwise attached to one or both sides of PA/PU composite material 70, after which second shell 23 is assembled from the resulting material by RF welding. Second shell 23, which is fabricated of material with PU/EVOH/PE composite material 90 on both sides of PA/PU composite material 70, is typically less flexible than a shell fabricated of material with a single sheet of PU/EVOH/PE composite material (as shown in FIG. 11).

Figure 13:
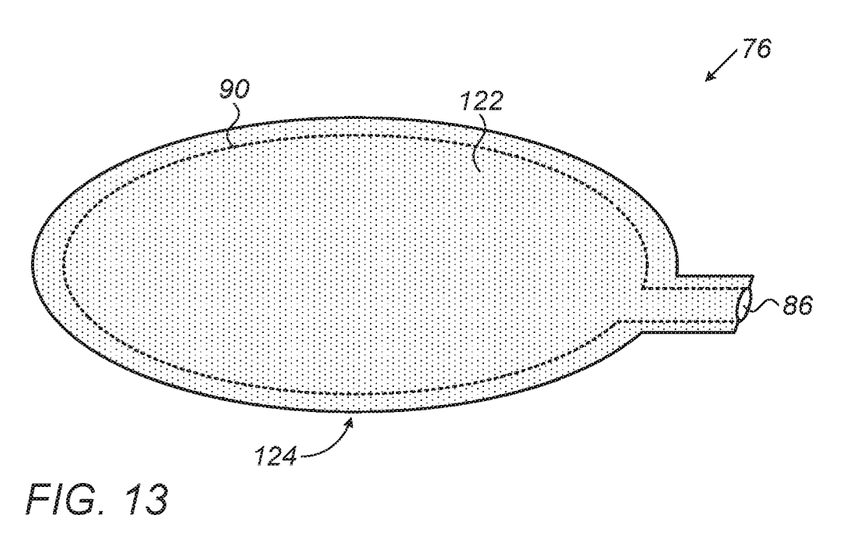
FIG. 13 is a schematic perspective view of a coated second shell preform, in accordance with an embodiment of the invention.
Figure 14:
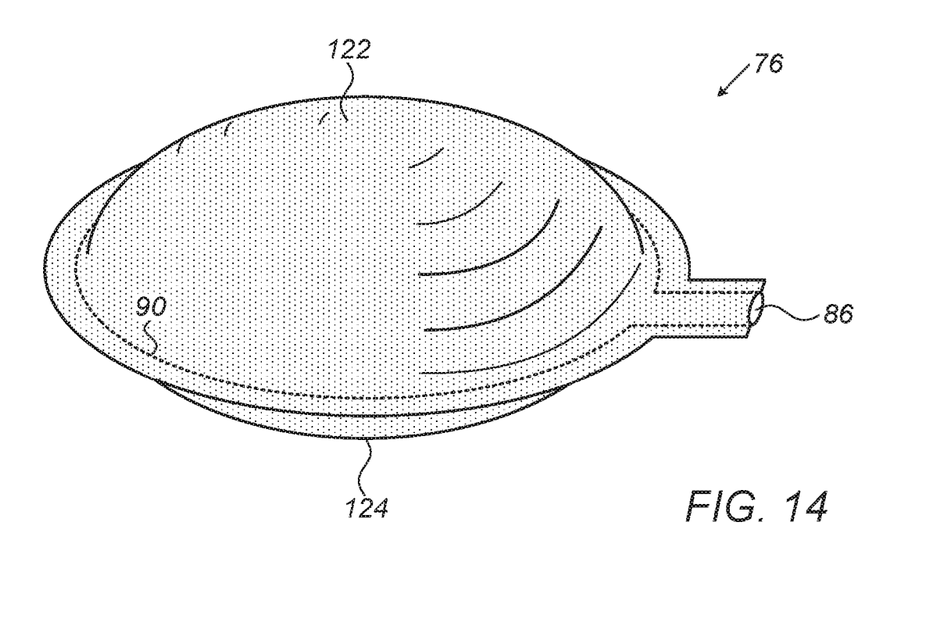
FIG. 14 is a schematic perspective view of the second shell preform after the preform has been inflated with air or other gas, in accordance with an embodiment of the invention.
Figure 15:
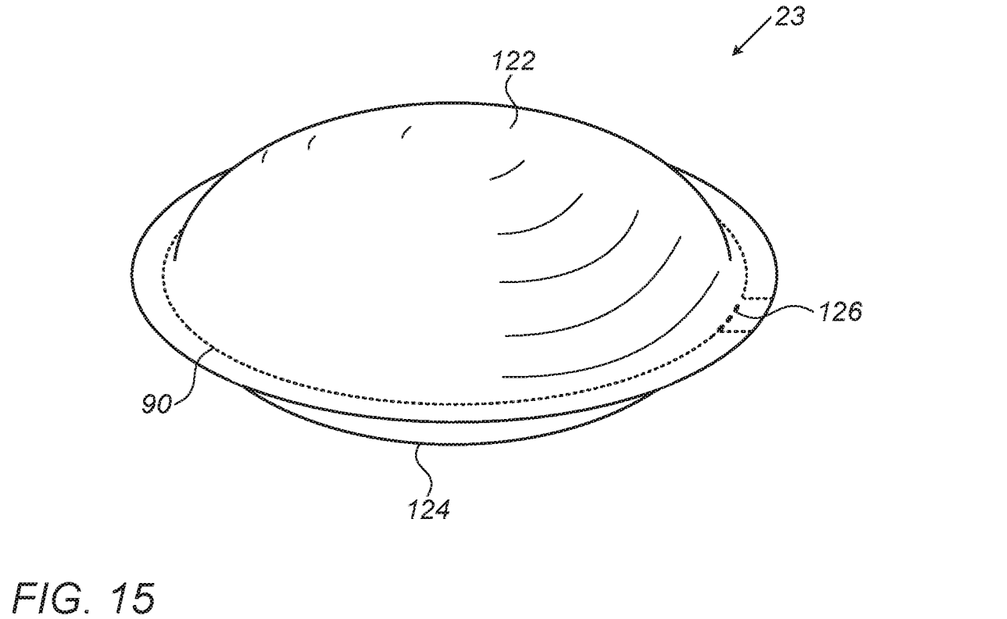
FIG. 15 is a schematic perspective view of a completed second shell formed from preform, in accordance with an embodiment of the invention.

FIGS. 13-15 show the construction of second shell 23 using a gas-impermeable coating, in accordance with an embodiment of the invention.

FIG. 13 is a schematic perspective view of coated second shell preform 76, in accordance with another embodiment of the invention. Coated second shell preform 76 is a result of depositing an impermeable coating as an upper coating 122 and a lower coating 124 on both sides of second shell preform 76 of FIG. 5.

In a first alternative embodiment of the coating, the deposition comprises spraying graphene oxide in a water dispersion onto second shell preform 76, and allowing it to dry. Graphene oxide in water dispersion is available from Graphenea, Paseo Mikeletegi 83, 20009 San Sebastián, SPAIN.

In a second alternative embodiment, the deposition comprises spraying aluminum oxide in a water dispersion onto second shell preform 76, and allowing it to dry. Aluminum oxide in water dispersion is available from, for example, American Elements, 10884 Weyburn Avenue, Los Angeles, Calif. 90024, USA.

In a third alternative embodiment, the deposition comprises spraying titanium oxide in a water dispersion onto second shell preform 76, and allowing it to dry. Titanium oxide in water dispersion is available from, for example, US Research Nanomaterials, Inc., 3302 Twig Leaf Lane, Houston, Tex. 77084, USA.

For all three suspensions of graphene oxide, aluminum oxide, and titanium oxide, more than one spray coating may be applied in order to attain sufficient impermeability. The spray coating is allowed to dry between successive applications.

After drying, each of the three oxides forms gas impermeable upper and lower coatings 122 and 124, respectively. All three oxides used as alternative embodiments in the coating (graphene oxide, aluminum oxide, and titanium oxide) are fully biocompatible.

FIG. 14 is a schematic perspective view of second shell preform 76 after the preform has been inflated with air or other gas, in accordance with an embodiment of the invention. Upper composite sheet 80 with coating 122 and lower composite sheet 82 with coating 124 have formed a balloon-like volume due to the inflation of second shell preform 76 through fill tube 86.

FIG. 15 is a schematic perspective view of completed second shell 23 formed from preform 76 of FIG. 14, in accordance with an embodiment of the invention. RF weld 90 has been completed with a sealing RF weld 126, thus completely sealing off the gas volume within the balloon-like volume. In addition, the part of fill tube 86 outside the edge of second shell preform 76 has been cut off.

Figure 16:
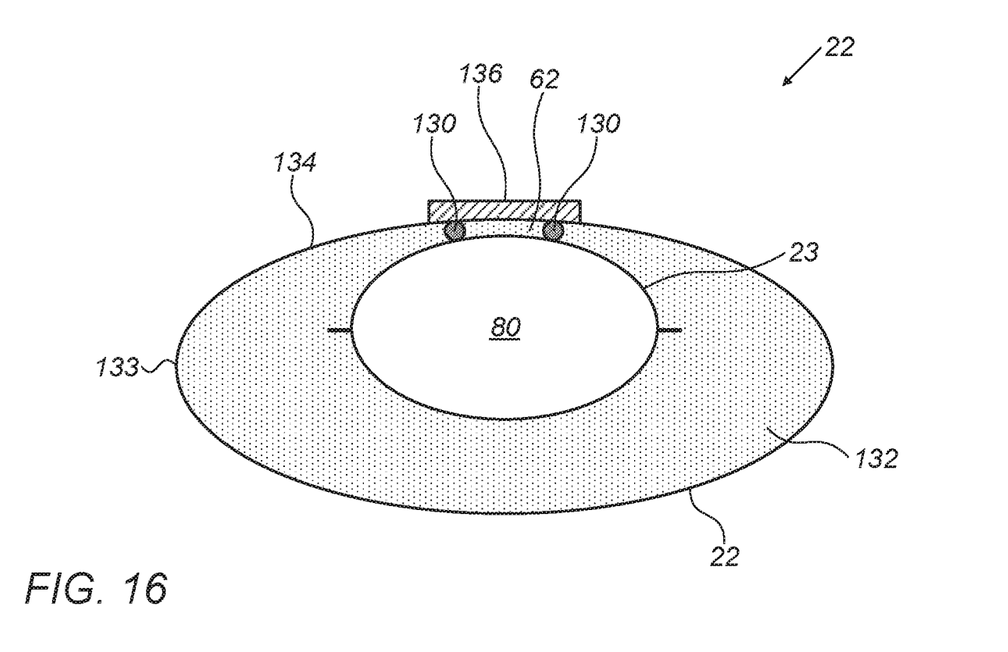
FIG. 16 is a schematic sectional view of a completed breast implant, in accordance with an embodiment of the invention.

FIG. 16 is a schematic sectional view of completed breast implant 21, in accordance with an embodiment of the invention. Completed second shell 23 (as described with reference to FIG. 10 or FIG. 15) has been inserted into first shell 22 (FIG. 2) through opening 62. Second shell 23 is further secured in place by a ring of cement 130, which attaches the second shell to first shell 22. Cement 130 also closes off the inside of first shell 22, thus enabling the subsequent filling of the first shell without leakage of the fill material, as will be described below. Instead of cement 130, other methods may be used for securing second shell 23 to first shell 22. Elements 132, 133, 134, and 136 are described further below.

Breast implant 21 is depicted in FIG. 16 as having the cross-sectional shape of an oval. However, due to the flexibility of the material of first shell 22 and completed second shell 23, as well as the elasticity of filler material 132, it will adapt its shape according to the surrounding tissue as shown in FIG. 1.

Figure 17:
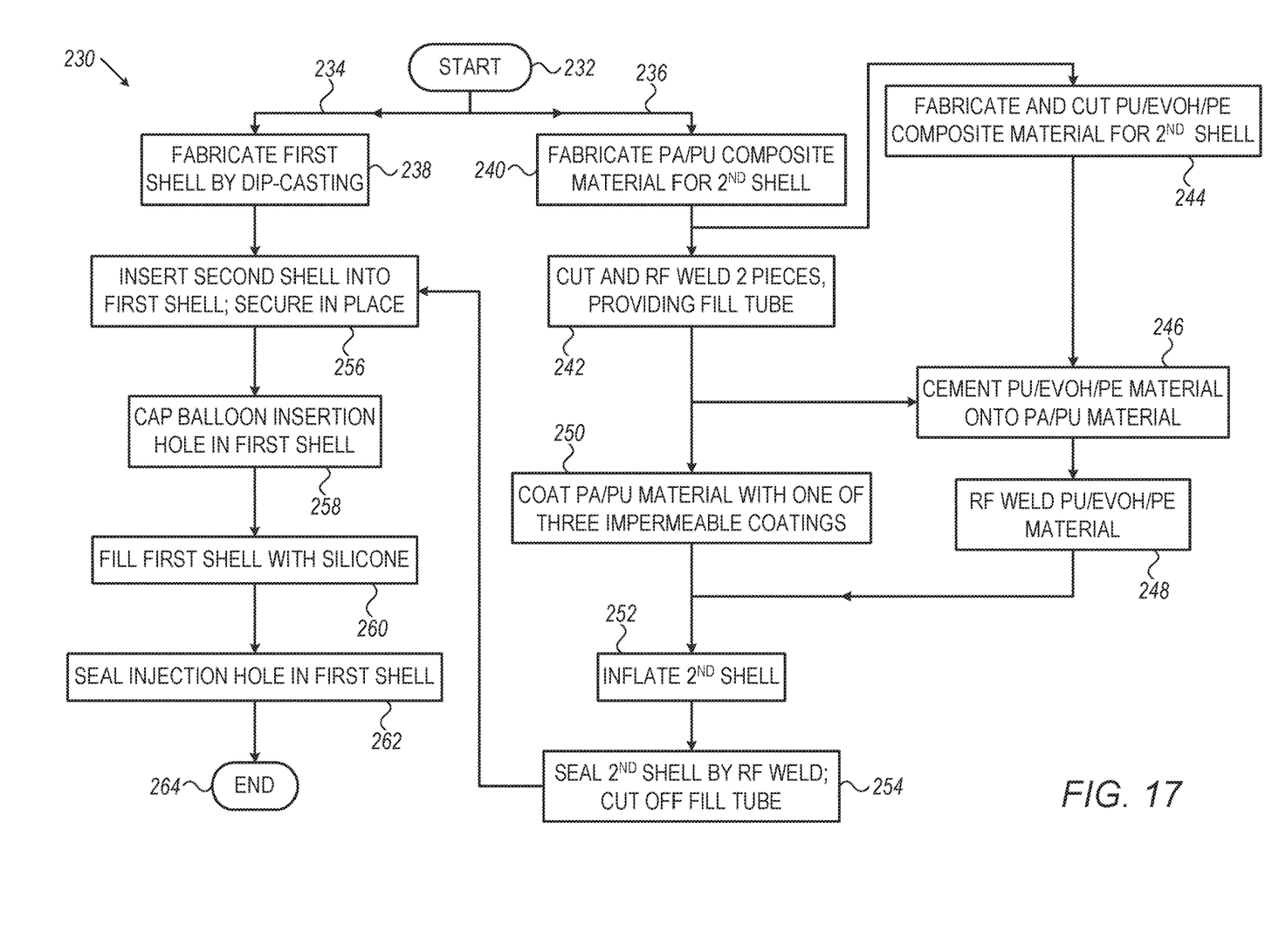
FIG. 17 is a flowchart that schematically illustrates a method for fabricating the breast implant, in accordance with embodiments of the invention.

FIG. 17 is a flowchart 230 that schematically illustrates a method for fabricating breast implant 21, in accordance with embodiments of the invention. The method splits into two paths 234 and 236 from a start step 232. Path 234 leads to a first shell fabricating step 238, which comprises the fabrication of first shell 22 by dip-casting as described above with reference to FIG. 2. Path 236 leads to steps 240-254 for fabricating second shell 23.

In a first material fabrication step 240 PA/PU composite material 70 for second shell 23 is fabricated as described above with reference to FIG. 3. In a cut and weld step 242, two pieces 80 and 82 of composite material 70 are cut to shape and attached to each other to form second shell preform 76 with fill tube 86 as described above with reference to FIGS. 4-5.

After first cut and weld step 242, the process splits into alternative embodiments, with the first comprising steps 244-248 and the second comprising step 250.

In the first alternative embodiment, in a second material fabrication step 244 PU/EVOH/PE composite material 90 is fabricated and cut to sheets 100 and 102 as described above with reference to FIGS. 6-7. With reference to FIG. 8, in an EVOH cementing step 246, sheets 100 and 102 are cemented to second shell preform 76 from first cut and weld step 242. With further reference to FIG. 8, in a weld step 248 sheets 100 and 102 are RF welded to each other.

In the second alternative embodiment, in a coat step 250 second shell preform 76 from first cut and weld step 242 is coated by one of three impermeable coatings, as described above with reference to FIG. 13.

The alternative embodiments described above now converge and continue in an inflation step 252, where second shell preform 76 is inflated with gas as described above with reference to FIGS. 9 and 14. In a seal step 254 inflated second shell preform 76 is sealed with an RF weld and fill tube 86 is cut off as described above with reference to FIGS. 10 and 15. The result of seal step 254 is completed second shell 23.

Step 238 and steps 240-254 may be implemented serially or in parallel. These steps converge in a second shell insertion step 256, where completed second shell 23 is inserted and secured in first shell 22 as described above with reference to FIG. 16. Further referencing FIG. 16, in a cap step 258 a cap 136 of the same material as first shell 22 is used to close opening 62. The use of cap 136, in addition to cement 130, further secures implant 21 against leaks of elastic filler material 132.

In an implant fill step 260 first shell 22 is filled with an elastic filler material 132 using a syringe (not shown) through a shell wall 133 at a location 134, until a predetermined volume of material has been injected. After implant filling step 260, the silicone gel is set, typically at an elevated temperature of approximately 160° C.

After completing the injection of the material, the injection hole at location 134 is sealed in a seal step 262 using the same material as used for fabricating first shell 22. A typical volume of breast implant 21 is 800 cc. Were second shell 23 not inserted into first shell 22, the entire 800 cc volume would be filled with elastic filler material 132, weighing approximately 800 g. The volume of the second shell is typically 30-40% of the total volume of breast implant 21, leading to a reduction of the injected elastic filler material 132 by 30-40% of the volume of 800 cc, which in turn reduces the weight of the implant by 30-40% of the weight of 800 g.

Elastic filler material 132 typically comprises a 2-component silicone gel. The silicone gel is a viscose liquid while being injected through the syringe. Before the silicone gel is injected into first shell 22, air bubbles are removed from the gel under vacuum.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An implantable device, comprising:
    a first sealed flexible shell configured for implantation within a breast of a human subject;
    an elastic filler material contained within the first sealed flexible shell;
    a second sealed flexible, inelastic shell, which is disposed within the elastic filler material inside the first sealed flexible shell and is inflated with a volume of a gas, wherein the second shell is constructed of a substance impermeable to the gas, such that an amount of the gas escaping from the second shell does not exceed $10^{-8}$ Torr-liter/second when the gas pressure inside the second shell is 250 mbar higher than the gas pressure outside the second shell;

wherein the second sealed flexible, inelastic shell comprises a first composite comprising polyamide and polyurethane, and a second composite comprising polyurethane and ethylene vinyl alcohol.

2. The implantable device according to claim 1, wherein at least one coating impermeable to the gas is deposited on the second shell.

3. The implantable device according to claim 2, wherein the coating comprises graphene oxide.

4. The implantable device according to claim 2, wherein the coating comprises aluminum oxide.

5. The implantable device according to claim 2, wherein the coating comprises titanium oxide.

6. The implantable device according to claim 1, wherein the elastic filler material comprises silicone gel.

7. The implantable device according to claim 1, wherein the volume of gas comprises a volume of air.

8. The implantable device according to claim 1, wherein the volume of gas comprises a volume of argon.

* * * * *